United States Patent [19]

Tobias

[11] 4,237,616
[45] Dec. 9, 1980

[54] SCANNING PATH ALIGNMENT ARRANGEMENT

[76] Inventor: Philip E. Tobias, 1872 Watson Rd., Abington, Pa. 19001

[21] Appl. No.: 951,148

[22] Filed: Oct. 13, 1978

[51] Int. Cl.³ .................... G01B 11/00; G01C 15/00
[52] U.S. Cl. ................................. 33/286; 356/399
[58] Field of Search .............. 356/399, 401; 33/184.5, 33/286

[56] References Cited

U.S. PATENT DOCUMENTS 2,290,586  7/1942  Gentry ............................ 33/184.5

Primary Examiner—John K. Corbin
Assistant Examiner—Bruce Y. Arnold
Attorney, Agent, or Firm—William E. Cleaver

[57] ABSTRACT

The present device includes a pair of wires which are located one above the other in a plane that lies parallel and orthogonal to the center lines of a path which a scanning head is going to view, as it travels in a scanning excursion. The wires are held taut and when they are in vertical alignment to the human eye (for convenience as reflected in a tilted mirror) then material to be scanned along a certain path can be centered under what appears to be "one wire" and in this way the scanning head will pass directly over the proper portion of the material.

2 Claims, 3 Drawing Figures

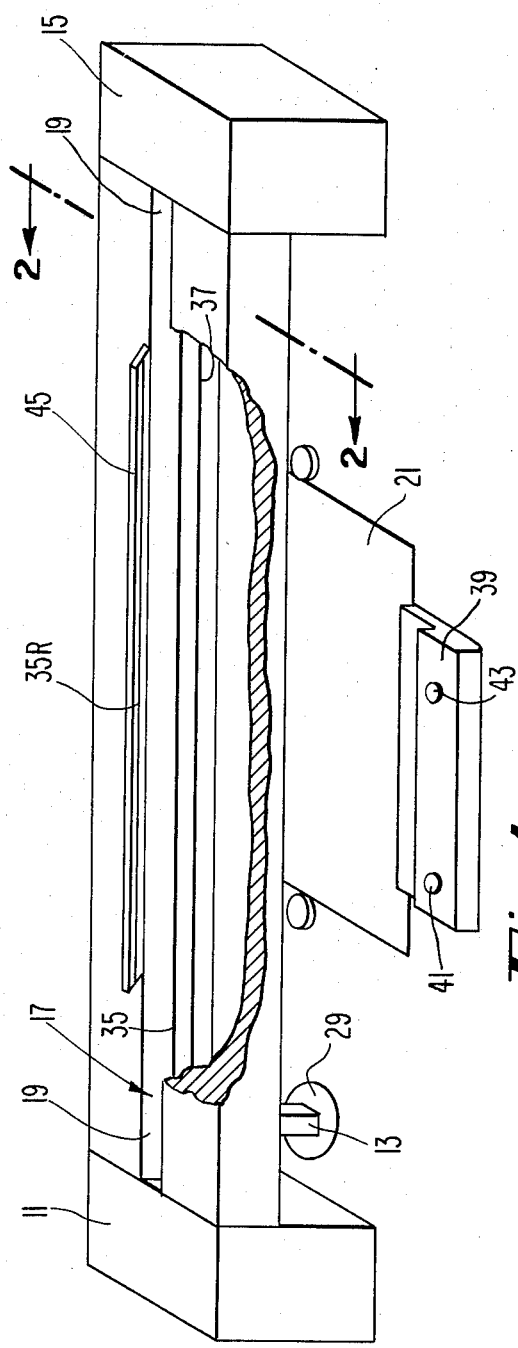
Fig. 1
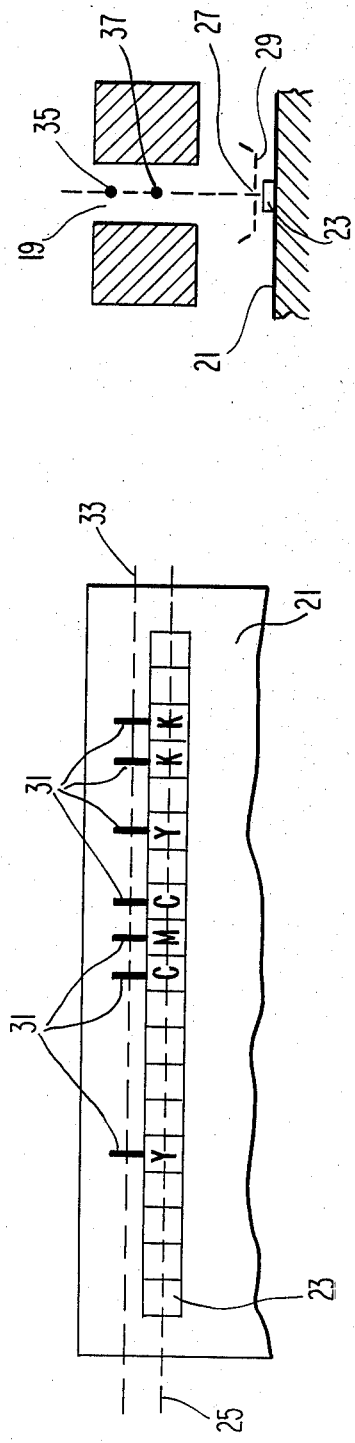
Fig. 2
Fig. 3

SCANNING PATH ALIGNMENT ARRANGEMENT

BACKGROUND

In my copending patent application, "Color Monitoring System For Use In Creating Colored Displays" Ser. No. 951,444 filed Oct. 13, 1978, a system is described wherein a scanning densitometer head is moved over a color swatch bar to read selected ones of the color swatches and automatically determine the color that it is viewing and record the optical density thereof. In order for the scanning head to make a meaningful excursion, the color swatch bar must be carefully located so that the light beam from the scanning head strikes each color swatch as close to the center as possible. When the user is going to effect a scan, he places the copy with the color swatch bar under a bridge-like arrangement along which the scanning head is moved by a belt. Unless he can somehow line the center line (as considered lengthwise) of the color swatch bar with the center of the aperture in the base of the scanning head, then the scanning run of the head is likely to read misinformation. With the present device the wires lie in a plane which intersects a line defined by the center point of the aperture of the scanning head and which plane lies orthogonal to the plane in which the base of the head lies.

SUMMARY

The present alignment arrangement makes it a simple matter for the user to align a color swatch bar, or a plurality of markers associated therewith on any pattern which is going to interact with a moving mechanism, such as being viewed by a scanning densitometer head. A first and second wire are located one above the other in the same plane. The plane is parallel to and orthogonal to the lengthwise center line of the pattern. When with his eye, the user aligns the two wires in the same plane, then he can readily locate the center line of the pattern thereunder and then the center line is in the proper location to be scanned by the scanning densitometer head. In a preferred embodiment there is a mirror held at a 45° angle to the plane in which the wires can be aligned and hence a viewer can align the wires in his view, even though he is looking from a vantage point which is at a right angle to said plane. In other words, the user can sit or stand in front of the machine and align the material for a good scan without having to walk to the end of the machine or climb on top of it to look down.

The objects and features of the present invention will be better understood from the description hereinafter taken in conjunction with drawings wherein:

FIG. 1 is a pictorial schematic showing the scanning densitometer head and a breakaway section of the housing to show the present invention; and FIG. 2 shows a sectionalized view of FIG. 1 along line 2—2; and FIG. 3 shows a color swatch bar and associated markers.

Consider FIG. 1. In FIG. 1 there is shown a portion of the scanning densitometer system described in my copending application "Color Monitoring System For Use In Creating Colored Displays" as mentioned earlier. The console and video display are not shown in FIG. 1. In FIG. 1 there is shown an end box 11 in which there is housed the drive motor which drives the belt to which the scanning head 13 is secured. The belt is not shown, to simplify the drawing. The belt travels around an idle pulley in end housing 15.

If we were to view the assembly shown in FIG. 1 from the top, as shown by arrow 17, we would find an open channel 19 which runs the length of the assembly and which permits the viewer to see the copy 21 from the top of the assembly.

If copy 21 had a color swatch bar thereon such as the color swatch bar 23 in FIG. 3 and we wanted to have the scanning densitometer head 13 scan that color swatch bar, then we should align the center line 25 of the color swatch bar 23 with the center of the aperture (see aperture 27 in the baffle 29 drawn in phantom in FIG. 2) of the scanning head 13. In this way, when the scanning head 13 passes over the color swatch bar 23, there would be a good reading of the reflected light from the color swatches. In FIG. 2 it can be noted that opposite the color swatches marked Y (yellow), C (cyan), M (magenta) and K (black) there are placed black markers 31. The scanning densitometer system of my above-mentioned patent application uses such markers to provide a reference for the swatches that the system should scan. When the scanning head 13 sees a marker, it detects it as a black marker, and the logic circuitry in the system (along with the proper program instructions) remembers where the markers are in the excursion. Thereafter when the system is going to scan the color swatch bar and the copy 21 is moved up, the system will alert the logic circuitry to particularly examine the signals from the scanning head when the marker positions are reached.

With respect to the present invention it is important that if the user is going to do a scan of the black markers that the copy be aligned so that the scanning head 13 passes centrally along the center line 33 through the markers.

In order to make the alignment of the copy relatively easy, there are two wires 35 and 37 located in the channel 19, as can be seen in FIGS. 1 and 2. The wires 35 and 37 are located in a single plane with wire 35 above wire 37 and wire 35 lying further away from the center line 25 through the color swatch bar 23. The ink of swatch bar 23 is shown greatly exaggerated in FIG. 2 so that the relationship between the wires 35 and 37 and the color swatch bar 23 can be appreciated. The wires 35 and 37 are held taut by eye bolts which can be tightened but other means to hold said wires taut can be used. In FIG. 2 the baffle 29 is shown in phantom so that the relationship between the wires 35 and 37 and the aperture in the scanning head 13 can be appreciated.

When the copy 21 is to be moved or located so that the color swatch bar 23 is properly aligned with the scanning head 13 the user can view the two wires 35 and 37 until they become "one wire" to the users eye. If copy 21 is moved at that time until the viewer sees equal amounts of the color swatches on both sides of the "one wire" then wires 35, 37 and center line 25 will be in the same plane. At that time the guide bar 39 is secured to the base by the magnet means 41 and 43 to keep copy 21 in proper alignment for the scanning head.

Since it may be awkward for the viewer to look from the top of channel 19 to align the wires 35 and 37 by eye, the present arrangement provides a mirror 45 as seen in FIG. 1. The mirror 45 is disposed at an angle of 45° to the plane in which wires 35 and 37 lie when perpendicular to the center line 25. Hence a user can sit or stand in front of the system (on the guide bar 39 side)

and see the reflection of the wires 35 and 37 in the mirror 45. The user can align the wires 35 and 37 as seen in the mirror 45 and when he sees them as "one wire" he locates his center line 25 thereunder. In FIG. 1 the wires 35 and 37 are shown as "one wire" 35R.

Accordingly the present wire arrangement, particularly with the use of the mirror, provides a means to readily align a pattern on a sheet of material with the path of a moving mechanism, such as a scanning head.

What I claim is:

1. An alignment arrangement for aligning material along a path which the projection of a moving mechanism will follow in order for the moving mechanism to have an interaction with said material comprising in combination: first wire means disposed in a plane which lies parallel to said path and orthogonal to the center line of said path; second wire means disposed in said last mentioned plane and additionally disposed to lie further away from said center line of said path than said first wire; and means to hold said wires taut so that when by human eye said second wire is aligned directly over said first wire the center line of the path on said material can be located to be in alignment with said plane as defined by the alignment of said first and second wires.

2. An alignment arrangement according to claim 1 wherein there is further included a mirror means whose reflection surface is disposed at 45° angle to the plane in which said first and second wires are located when in alignment with said center line of said path.

* * * * *